United States Patent
Camarero et al.

(10) Patent No.: US 7,700,334 B2
(45) Date of Patent: Apr. 20, 2010

(54) PHOTOSWITCHABLE METHOD FOR THE ORDERED ATTACHMENT OF PROTEINS TO SURFACES

(75) Inventors: Julio A. Camarero, Livermore, CA (US); James J. De Yoreo, Clayton, CA (US); Youngeun Kwon, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 161 days.

(21) Appl. No.: 11/688,171

(22) Filed: Mar. 19, 2007

(65) Prior Publication Data

US 2007/0225482 A1 Sep. 27, 2007

Related U.S. Application Data

(63) Continuation-in-part of application No. 10/918,759, filed on Aug. 12, 2004, now abandoned.

(60) Provisional application No. 60/494,675, filed on Aug. 12, 2003.

(51) Int. Cl.
 *C12N 11/02* (2006.01)
 *A61K 38/00* (2006.01)

(52) U.S. Cl. .................. 435/177; 435/174; 435/181; 530/300; 530/402

(58) Field of Classification Search .................. None
See application file for complete search history.

(56) References Cited

U.S. PATENT DOCUMENTS

| 5,489,678 | A | * | 2/1996 | Fodor et al. ................ 506/30 |
| 5,496,714 | A | * | 3/1996 | Comb et al. ............... 435/69.7 |
| 6,197,599 | B1 | * | 3/2001 | Chin et al. ................. 436/518 |
| 7,405,276 | B2 | * | 7/2008 | Himawan ................ 530/387.3 |
| 2002/0177691 | A1 | * | 11/2002 | Scott et al. ................. 530/350 |

FOREIGN PATENT DOCUMENTS

| WO | WO 01/98456 A2 | 12/2001 |
| WO | WO 0198458 A2 | * | 12/2001 |

OTHER PUBLICATIONS

Blawas et al. (1998) Protein patterning, Biomaterials, vol. 19, issues 7-9, pp. 595-609.*
Ror et al. (2001) Local photorelease of caged thymosin beta4 in locomoting keratocytes causes cell turning, J. Cell Biol., vol. 135, No. 5, pp. 1035-1248.*
Fang et al. (2002) Membrane Protein Microarrays, J. Am. Chem. Soc., vol. 124, No. 11, pp. 2394-2395.*
Lam et al. (2002) From combinatorial chemistry to chemical microarray, Curr. Opin. Chem. Biol., vol. 6, No. 3, pp. 353-358.*
Wu et al. (1998) Protein trans-splicing by a split intein encoded in a split DnaE gene of *Synechocystis* sp. PCC6803, Proc. Natl. Acad. Sci. U S A., vol. 95, No. 16, pp. 9226-9231.*
Mills et al. (2006) Protein purification via temperature-dependent, intein-mediated cleavage from an immobilized metal affinity resin, Anal. Biochem, vol. 356, No. 1, pp. 86-93.*
Girish et al. (2005) Site-specific immobilization of proteins in a microarray using intein-mediated protein splicing, Bioorg. Med., Chem. Lett., vol. 15, No. 10, pp. 2447-2451.*
Martin et al. (2001) Characterization of a naturally occurring trans-splicing intein from *Synechocystis* sp. PCC6803, Biochemistry, vol. 40, No. 5, pp. 1393-1402.*
Evans et al. (2000) Protein trans-Splicing and Cyclization by a Naturally Split Intein from the dnaE Gene of *Synechocystis* Species PCC6803, J. Bio. Chem., vol. 275, No. 13, pp. 9091-9094.*
Camarero, J., et al., "Chemoselective Attachment of Biologically Active Proteins to Surfaces by Expressed Protein ligation and Its Aplication for "Protein Chip" Fabrication," J. Am. Chem. Soc., (2004), 126, pp. 14730-14731.
Camarero, J., "Introduction to Polypeptide Chemical Ligation Tools in Protein Engineering," Protein & Peptide Letters, (2005), vol. 12, No. 8, 2 pages.
Camarero, J., "New Developments for the Site-Specific Attachment of Protein to Surfaces," Biophysical Reviews and Letters, vol. 1, No. 1, (2006), pp. 1-28.
Kwon, Y., et al., "Selective Immobilization of Proteins onto a Solid Support Through Split-Intein Mediated Protein Trans-Splicing," Angewandte Chemie, (2006), 17 pages.
Kwon, Y., et al., "Selective Immobilization of Proteins onto Solid Supports through Split-Intein-Mediated Protein Trans-Splicing," Angew. Chem., Intl. Ed. (2006) 45, pp. 1-4.
Kwon, Y., et al., "Selective Immobilization of Proteins onto Solid Supports through Split-Intein-Mediated Protein Trans-Splicing," Angew. Chem. Int. Ed., (2006) 45, pp. 1726-1729.
Camarero, J., et al., "Synthesis of Proteins by Native Chemical Ligation Using Fmoc-Based Checmistry," Protein & Peptide Letters, (2005), 12, pp. 723-728.

\* cited by examiner

*Primary Examiner*—Anand U Desai
*Assistant Examiner*—Samuel Liu
(74) *Attorney, Agent, or Firm*—John H. Lee

(57) ABSTRACT

Described herein is a method for the attachment of proteins to any solid support with control over the orientation of the attachment. The method is extremely efficient, not requiring the previous purification of the protein to be attached, and can be activated by UV-light. Spatially addressable arrays of multiple protein components can be generated by using standard photolithographic techniques.

10 Claims, 6 Drawing Sheets

FIGURE 2A
FIGURE 2B
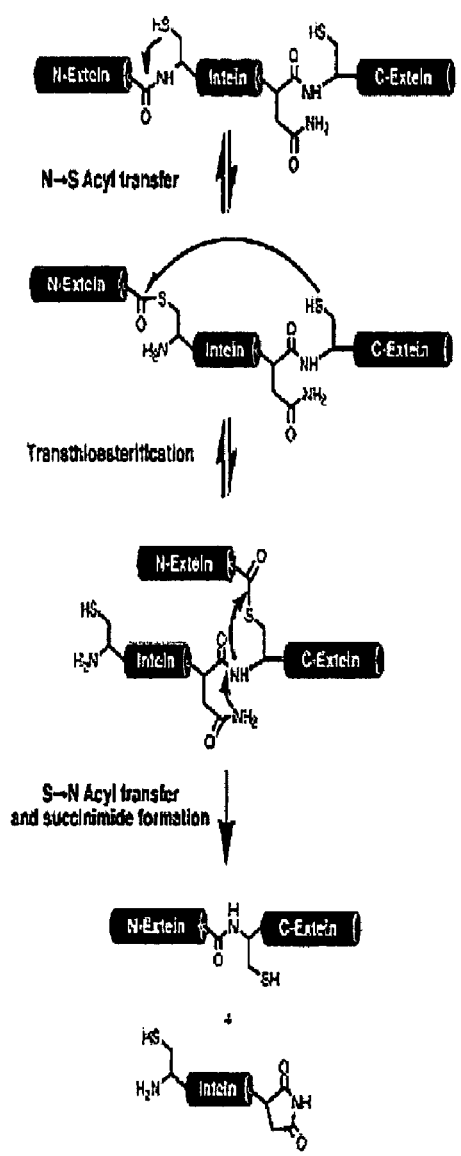
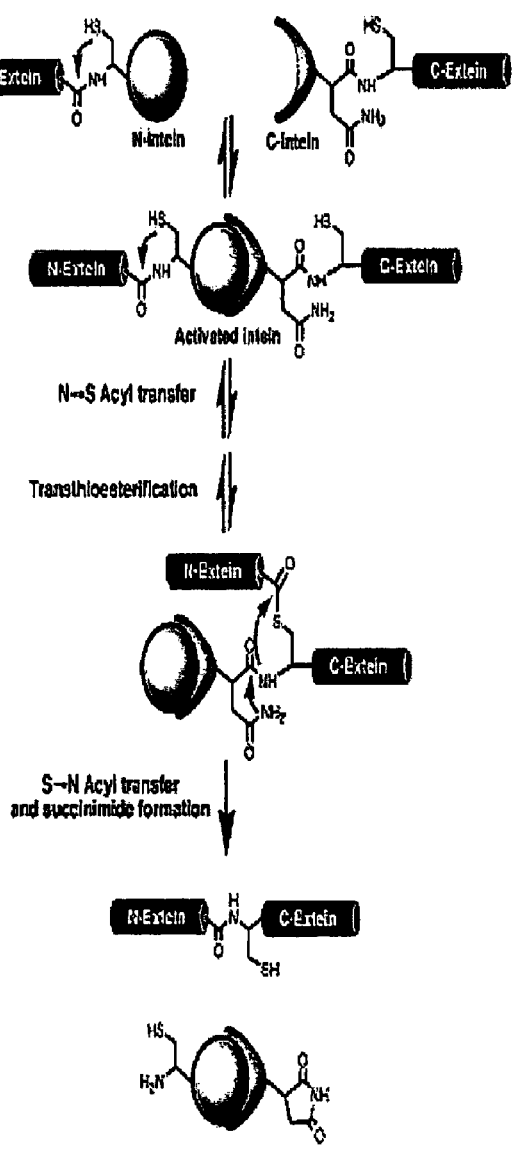

350 μm

Structural Model of the split DnaE-Intein

C-Intein Sequence

MVKVIGRRSLGVQRIFDIGLPQDHNFLLANGAIAANCFN

SEQUENCE LISTING

<160> NUMBER OF SEQ ID NOS: 9

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tggaattctt tgcggaatat tgcctcagtt ttgg                           34

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttggatcct tatttaattg tcccagcgtc aagtaatgga aaggg               45

<210> SEQ ID NO 3
<211> LENGTH: 123
<212> TYPE: PRT
<213> ORGANISM: Synechocystis sp.

<400> SEQUENCE: 3

Cys Leu Ser Phe Gly Thr Glu Ile Leu Thr Val Glu Tyr Gly Pro Leu
 1               5                  10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

```
Leu Glu Asn Ile Lys Gln Thr Glu Glu Ala Leu Asp Asn His Arg Leu
                100                 105                 110

Pro Phe Pro Leu Leu Asp Ala Gly Thr Ile Lys
        115                 120

<210> SEQ ID NO 4
<211> LENGTH: 36
<212> TYPE: PRT
<213> ORGANISM: Synechocystis sp.

<400> SEQUENCE: 4

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Asn
        35

<210> SEQ ID NO 5
<211> LENGTH: 39
<212> TYPE: PRT
<213> ORGANISM: Synechocystis sp.

<400> SEQUENCE: 5

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Asn Cys Phe Asn
        35

<210> SEQ ID NO 6
<211> LENGTH: 40
<212> TYPE: PRT
<213> ORGANISM: Synechocystis sp.

<400> SEQUENCE: 6

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Asn Cys Phe Asn Lys
        35                  40

<210> SEQ ID NO 7
<211> LENGTH: 127
<212> TYPE: PRT
<213> ORGANISM: Synechocystis sp.

<400> SEQUENCE: 7

Phe Ala Glu Tyr Cys Leu Ser Phe Gly Thr Glu Ile Leu Thr Val Glu
1               5                   10                  15

Tyr Gly Pro Leu Pro Ile Gly Lys Ile Val Ser Glu Glu Ile Asn Cys
            20                  25                  30

Ser Val Tyr Ser Val Asp Pro Glu Gly Arg Val Tyr Thr Gln Ala Ile
        35                  40                  45

Ala Gln Trp His Asp Arg Gly Glu Gln Glu Val Leu Glu Tyr Glu Leu
    50                  55                  60

Glu Asp Gly Ser Val Ile Arg Ala Thr Ser Asp His Arg Phe Leu Thr
65                  70                  75                  80
```

-continued

```
Thr Asp Tyr Gln Leu Leu Ala Ile Glu Glu Ile Phe Ala Arg Gln Leu
                 85                  90                  95

Asp Leu Leu Thr Leu Glu Asn Ile Lys Gln Thr Glu Glu Ala Leu Asp
            100                 105                 110

Asn His Arg Leu Pro Phe Pro Leu Leu Asp Ala Gly Thr Ile Lys
        115                 120                 125

<210> SEQ ID NO 8
<211> LENGTH: 4
<212> TYPE: PRT
<213> ORGANISM: Synechocystis sp.

<400> SEQUENCE: 8

Phe Ala Glu Tyr
 1

<210> SEQ ID NO 9
<211> LENGTH: 4
<212> TYPE: PRT
<213> ORGANISM: Synechocystis sp.

<400> SEQUENCE: 9

Cys Phe Asn Lys
 1
```

PHOTOSWITCHABLE METHOD FOR THE ORDERED ATTACHMENT OF PROTEINS TO SURFACES

CROSS REFERENCE TO RELATED APPLICATIONS

This application is a continuation-in-part of U.S. application Ser. No. 10/918,759, filed Aug. 12, 2004 (now abandoned), which is herein incorporated in its entirety by reference. U.S. application Ser. No. 10/918,759 is related to Provisional Application No. 60/494,675 filed Aug. 12, 2003 entitled "Chemoenzymatic-like and Photoswitchable Method for the Ordered Attachment of Proteins to Surfaces", and claims priority thereto under 35 USC 119(e). Provisional Application No. 60/494,675 is herein incorporated by reference in its entirety.

STATEMENT REGARDING FEDERALLY SPONSORED RESEARCH

The United States Government has rights in this invention pursuant to Contract No. W-7405-ENG-48 between the United States Department of Energy and the University of California for the operation of Lawrence Livermore National Laboratory.

BACKGROUND

Various methods are available for attaching proteins to solid surfaces. Most rely on either (1) non-specific adsorption, or (2) the reaction of chemical groups within proteins (e.g., amino and carboxylic acid groups) with surfaces containing complementary reactive groups. In both cases the protein is attached to the surface in random orientations. The use of recombinant affinity tags addresses the orientation issue, but the interactions of the tags are often reversible. Therefore, the recombinant affinity tags require large mediator proteins in order to remain stable over the course of subsequent assays.

Methods for the chemoselective attachment of proteins to surfaces have been developed. (See J. A. Camarero, "Chemoselective Ligation Methods for the Ordered Attachment of Proteins to Surfaces", in Solid-fluid Interfaces to Nanostructural Engineering, J. J. de Yoreo, Editor. 2004, Plenum/Kluwer Academic Publisher: New York and C. L. Cheung et al., Fabrication of Assembled Virus Nanostructures on Templates of Chemoselective Linkers Formed by Scanning Probe Nanolithography, J. Am. Chem. Soc. 125, p. 6848, 2003.) These methods rely on the introduction of two unique and mutually reactive groups on the protein and the support surface. The reaction between these two groups usually gives rise to the selective attachment of the protein to the surface with total control over the orientation. However, these methods, although highly selective, rely on uncatalyzed pseudo-bimolecular reactions with little or no entropic activation at all. This lack of entropic activation means that the efficiency of these bimolecular-like reactions will depend strongly on the concentration of the reagents (i.e., the protein to be attached).

BRIEF DESCRIPTION OF THE DRAWINGS

FIGS. 2A and 2B illustrates proposed mechanisms for protein splicing (FIG. 2A) and trans-splicing (FIG. 2B).

DETAILED DESCRIPTION

In the approach described herein, the intrinsic entropic barrier is overcome and attachment reactions are more efficient and selective, even under high dilution conditions, through the use of a highly selective molecular recognition event to bring together the two reactive species. This event will increase dramatically the local effective concentration of both reacting species thus accelerating the corresponding attachment reaction even under unfavorable conditions (i.e., low concentration and even in the presence of other proteins).

Figure 1:
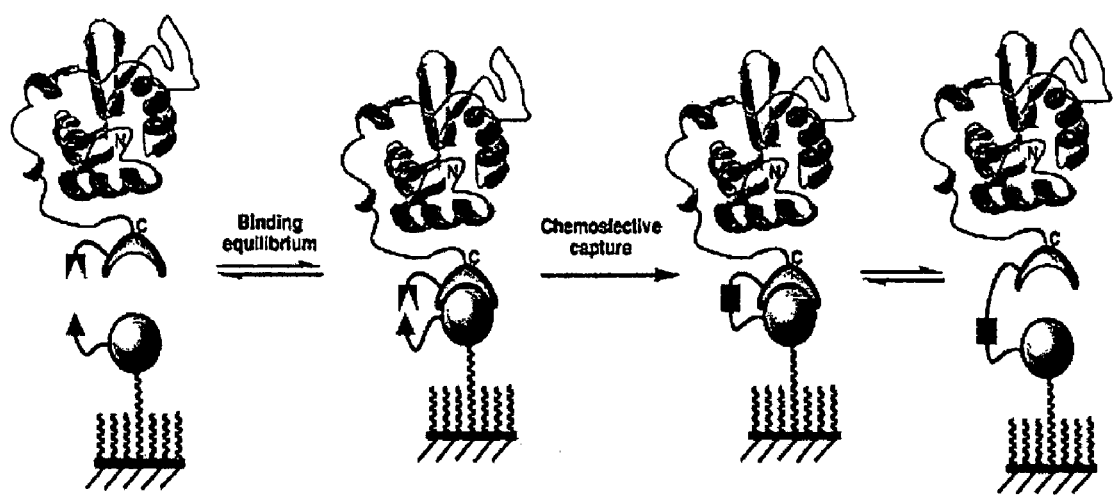
FIG. 1 illustrates the principle for selective immobilization of protein onto solid supports using an affinity assisted chemoselective reaction.

Referring to FIG. 1, this entropic activation approach can also be used to improve the efficiency and rate of attachment of proteins to surfaces with total control over the orientation of the attachment. Considerably less protein is required since the ligation reaction works very efficiently even under high dilution conditions. There is no need for purification since at high dilution the only protein that will react with the surface will be the one having the complementary affinity and reactive tag. The introduction of complementary moieties in the protein and the surface form a stable and specific intermolecular complex. Once formed, this complex can permit a selective reaction of the complementary chemical groups leading to the covalent attachment of the protein to the surface.

Disclosed herein is a photo-switchable method for the selective attachment of proteins through the C-terminus. The method is based on the protein trans-splicing process as shown in FIG. 2B. This process is similar to the protein splicing disclosed by Xu and co-workers (M.-Q. Xu et al. 1996 The mechanism of protein splicing and its modulation by mutation, EMBO J. 15(19), 5146-5153), which is shown in FIG. 2A. In the trans-splicing method disclosed herein, the intein self-processing domain is split in two fragments (called N-intein and C-intein, respectively). These two intein fragments alone are inactive, however, when they are put together under the appropriate conditions they bind specifically to each other yielding a totally functional splicing domain, which splices itself out at the same time that both extein sequences are ligated together.

In the method disclosed herein, the C-intein is chemically synthesized and covalently attached to a solid surface, e.g., a glass slide, through a small polyethylene glycolylated (PEGylated) linker. In some embodiments, the C-terminus of the C-intein includes 4 amino acid residues of the following extein. The C-intein is protected, e.g., photocaged, at a residue that interferes with trans-splicing. The N-intein is fused to the C-terminus of the protein of interest, e.g., as a recombinant fusion protein. In some embodiments, the N-terminus of the N-intein includes 4 amino acid residues of the preceding extein. The solid surface is contacted with the N-intein fusion protein, e.g., the N-intein fusion protein is spotted on the glass slide that is functionalized with the C-intein. No interaction occurs until the C-intein is deprotected, e.g., exposed to light. Discrete locations, e.g., addresses, can be exposed to light using methods well-known to one of skill in the art, e.g., using masking lithography. Once the C-intein is deprotected, the intein fragments interact at that location and form the active intein which ligates the protein of interest to the surface at the same time the split intein is spliced out into solution.

The solid surface can be any of those well-known to one of skill in the art, including but not limited to glass slides or silicon chips.

The split DnaE intein from Synechocystis sp. PCC6803 is a naturally occurring split intein that was first discovered by Liu and co-workers (H. Wu et al., Protein trans-splicing by a split intein encoded in the split DnaE gene of Synechocystis sp. PCC6803, Proc. Natl. Acad. Sci. USA 95, 9226-9231 (1998)). It was also predicted through sequence analysis in an independent study by Gorbalenya. In contrast with other inteins engineered to act as trans-splicing elements, which only work after a refolding step, the C— and N-intein fragments of the DnaE intein are able to self-assemble spontaneously without any refolding step. The DnaE split intein comprises an N-intein fragment having 123 residues (see FIG. 2B, Int-n, of Wu et al (1998) PNAS 95:9226; and Table 1, below, SEQ ID NO:3) and a C-intein fragment of 36 residues (see FIG. 2B, Int-c, of Wu et al (1998) PNAS 95:9226; and Table 1, below SEQ ID NO:4).

Kwon and co-workers have successfully used the split DnaE intein from Synechocystis sp. PCC6803 to selectively immobilize proteins onto solid surfaces (Kwon et al (2006) Selective Immobilization of proteins onto solid supports through split-intein mediated protein trans-splicing. Angew. Chem. Int. Ed. 45:1726-1729).

In the method described herein, a recombinant fusion protein is expressed where the DnaE N-intein fragment is fused to the C-terminus of the protein to be attached to the surface. The C-intein fragment is synthesized as a synthetic peptide by using a Solid-Phase Peptide Synthesis (SPPS) approach. This allows the introduction of polyethyleneglycolated (PEGylated) alkylthiol moiety at the C-terminus of the C-intein peptide which is used for attachment to solid surfaces (e.g., gold or Si-based).

Figure 4A:
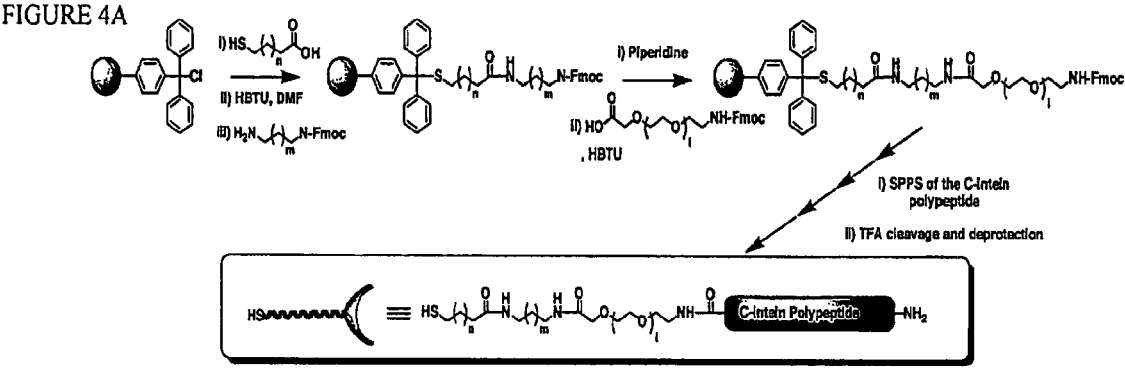
FIG. 4A illustrates a synthetic scheme for the rapid and efficient preparation of chemically modified thioalkanes containing a polyethyleneglycol (PEGylated) DnaE C-intein polypeptide.
Figure 4B:
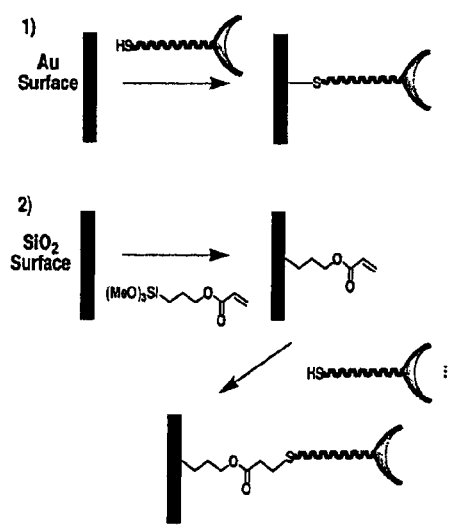
FIG. 4B illustrates selective immobilization of PEGylated DnaE C-intein polypeptide onto gold or acryloxy-containing Si-based substrates.

As illustrated in FIG. 4A, Fmoc-based solid-phase peptide synthesis of the C-intein can be performed on a PEGylated linker resin. After cleavage from the resin, the C-intein polypeptide is linked through its C-terminus through a PEGylated thiol linker. As illustrated in FIG. 4B, the linker serves as a spacer and can be used to chemoselectively attach the C-intein polypeptide to either gold or Si-based solid supports through its C-terminus.

Figure 5A:
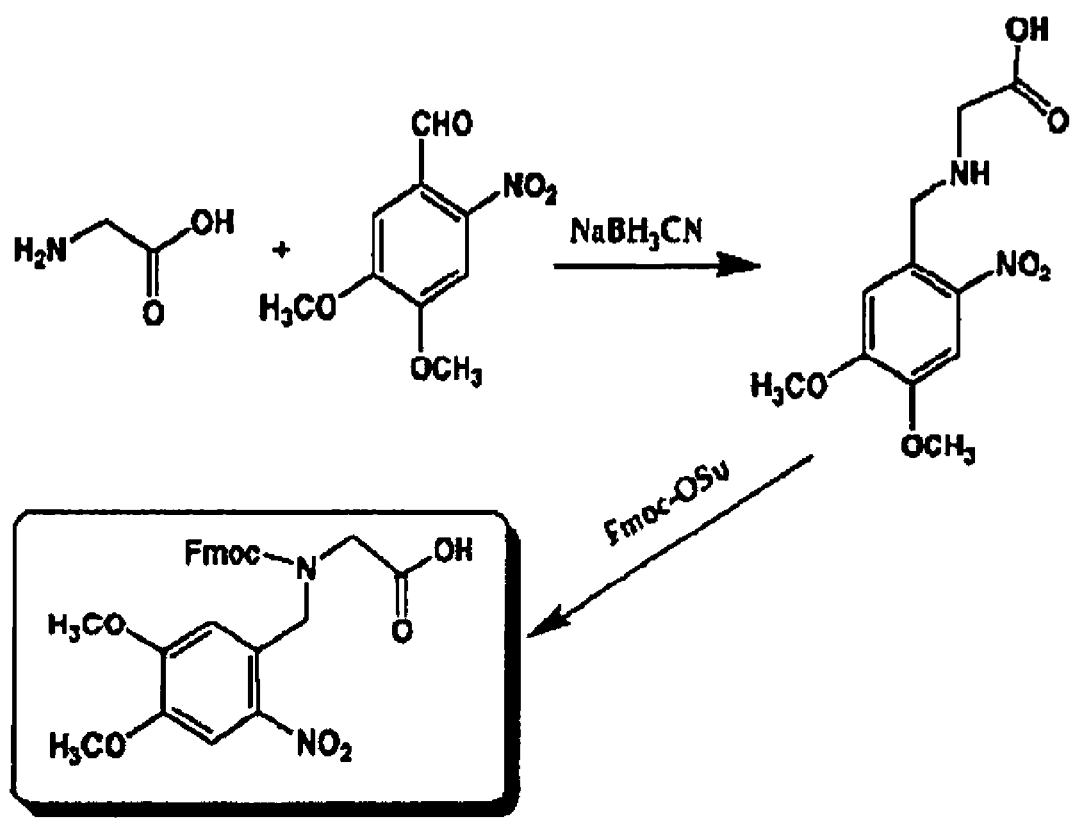
FIG. 5A illustrates a synthetic scheme for obtaining Fmoc-Gly(Nv)-OH.
Figure 5B:
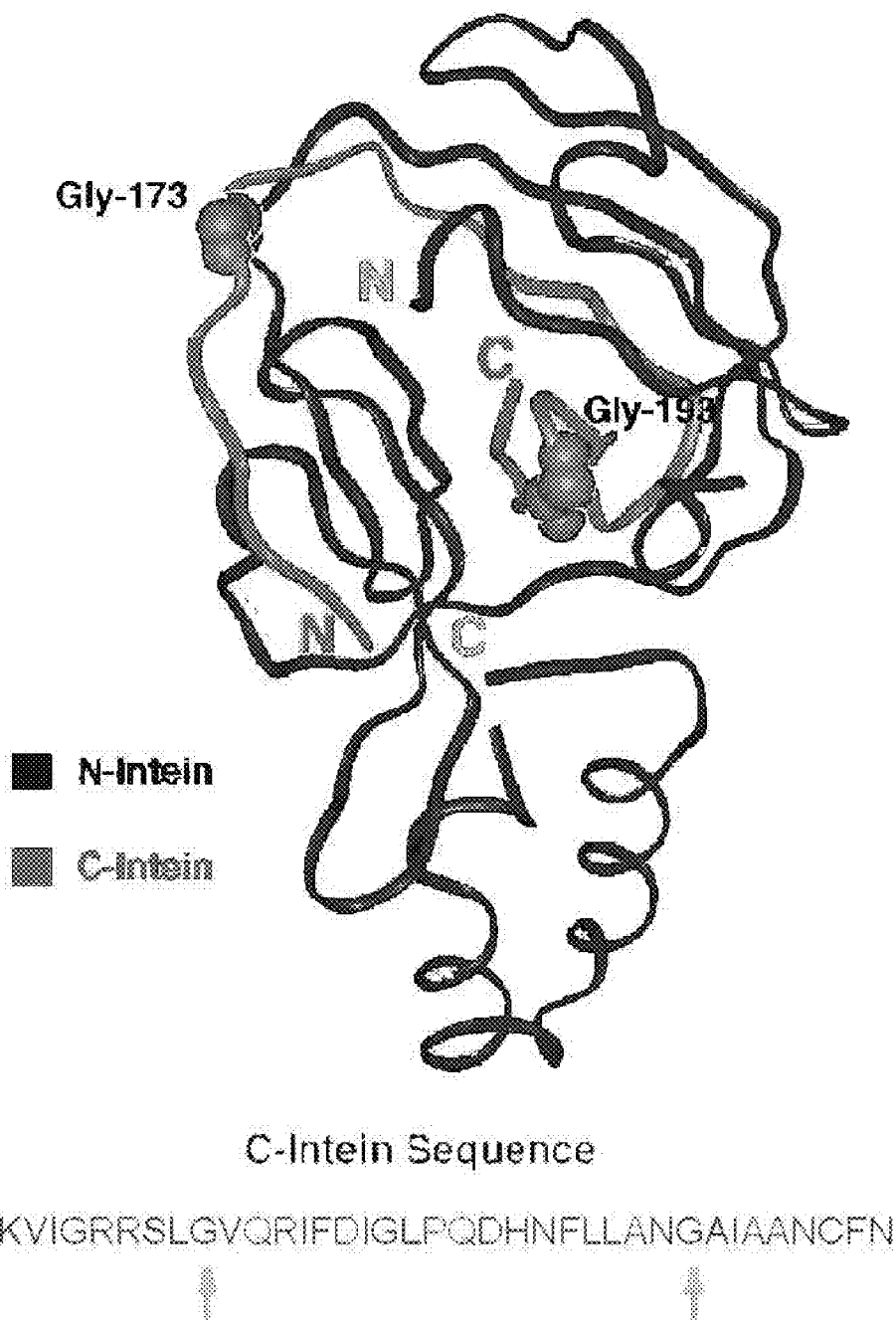
FIG. 5B is a structural model of the DnaE split intein based on the structure of the Mxe Gyrase A intein with the sequence of the DnaE C-intein polypeptide shown at the bottom of the figure (SEQ ID NO:5).

In addition, the synthesized C-intein polypeptide includes at least one protecting group, e.g., is photocaged. Photocaging allows spatially addressable protein arrays with multiple protein components to be created. One or more of the functional side-chains or backbone amide groups of a C-intein fragment key for the interaction with the N-intein are caged using a nitrobenzyl protecting group, such as the nitroveratryloxycarbonyl (Nvoc) or nitroveratryl (Nv). FIG. 5A shows the synthesis scheme of a backbone photocaged Gly residue for the solid-phase peptide synthesis of the photocaged C-intein. The Nv protecting group can be introduced into at least one Gly, Ala, Asn, Gln and Lys residues to prevent the interactions between the two intein fragments. For example, using the protecting group on the Gly residues 6, 11, 19 and/or 31 and/or Ala residues 29, 32, 34, and/or 35 is effective as is using the protecting group on the Asp residue 17 and/or 23, the Asn residues 25, 30 and/or 36, and/or the Gln residues 13 and/or 22. FIG. 5B is a structural model of the split DnaE-intein illustrating two of the Gly residues that can be photocaged in order to prevent the association of the C-intein and N-intein fragments.

Removal of the protecting group is achieved by exposure to UV-light (e.g., using a 10 µW pulse of 354-nm UV light generated from a He—Cd laser or similar source). When this photo-labile protecting group is removed by the action of UV-light, the two intein fragments assemble into a functional intein domain, thus allowing the attachment of the corresponding protein to the surface through protein splicing (See FIG. 3B). At the same time, both intein moieties are spliced out and consequently removed.

Figure 3A:
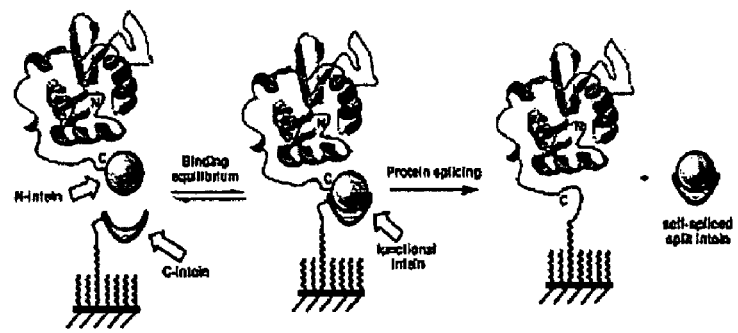
FIGS. 3A and 3B illustrates immobilization of proteins using the trans-splicing approach (FIG. 3A) and control of this approach using photocaging (FIG. 3B).
Figure 3B:
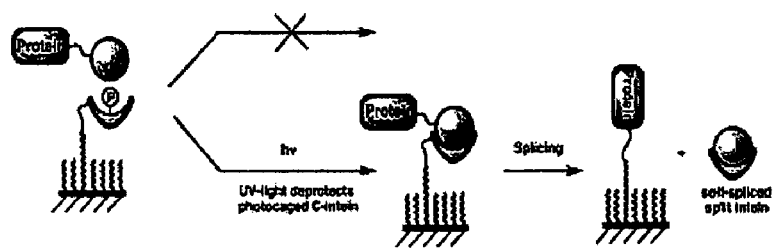

Referring to FIG. 3A, the C-intein fragment is attached to the solid surface and the N-intein fragment is fused to the C-terminus of the protein to be attached. When this fusion protein is exposed to a C-intein-containing surface, the two intein fragments associate yielding a fully operational intein domain that then splices out at the same time attaching the protein to the surface.

In some embodiments, extein amino acids are added to the C-intein and/or the N-intein to increase the efficiency of the trans-splicing event (Kwon et al (2006) Selective Immobilization of proteins onto solid supports through split-intein mediated protein trans-splicing. Angew. Chem. Int. Ed. 45:1726-1729). For example, extein residues FAEY (SEQ ID NO:8) are added to the N-terminus of the N-intein (see SEQ ID NO:7). Extein residues CFNK (SEQ ID NO:9) can be added to the C-terminus of C-intein (see SEQ ID NO:6).

EXAMPLES

Materials and Methods

Fmoc-amino acids, O-benzotriazol-1-yl-N,N,N',N'-tetramethyluronium hexafluoro-phosphate (HBTU) and 4-Fmoc-hydrazine AM resin were obtained from Novabiochem. Methylene chloride (DCM), N,N-dimethylformamide (DMF) and High Pressure Liquid Chromatography-grade (HPLC-grade) acetonitrile (MeCN) were purchased from Fisher. Trifluoroacetic acid (TFA) was purchased from Halocarbon. All other reagents were obtained from Aldrich Chemical Co. Analytical and semipreparative gradient HPLC were performed on a Hewlett-Packard 1100 series instrument with UV detection. Semipreparative HPLC was run on a Vydac C18 column (10 micron, 10×250 mm) at a flow rate of 5 mL/min. Analytical HPLC was performed on a Vydac C18 column (5 micron, 4.6×150 mm) at a flow rate of 1 mL/min. Preparative HPLC was performed on a Waters DeltaPrep 4000 system fitted with a Waters 486 tunable absorbance detector using a Vydac C18 column (15-20 micron, 50×250 mm) at a flow rate of 50 mL/min. All runs used linear gradients of 0.1% aqueous TFA (solvent A) vs. 90% MeCN plus 0.1% TFA (solvent B). $^1$H NMR spectra were obtained at room temperature on Bruker 400 MHz or Varian 90 MHz spectrometers. Electrospray mass spectrometric (ES-MS) analysis was routinely applied to all synthetic peptides and components of reaction mixtures. ESMS was performed on a Applied Biosystems/Sciex API-150EX single quadrupole electrospray mass spectrometer. Calculated masses were obtained using the program ProMac 1.5.3.

Synthesis of PEGylated Thiol Linker Resin.

Trityl resin (1 g, 1.1 mmol/g) was swollen in DCM for 20 min and washed with dimethylformamide (DMF) and then dichloromethane (DCM). 3-Mercaptopropionic acid (2 mmol, 175 μL mg) in DCM:DMF (4 ml, 9:1 v/v) was added to the swollen resin. The reaction was kept for 18 h at room temperature with gentle agitation. The reacted resin was then washed with DCM and DMF. The carboxylic function of the resin was activated with 2-[1H-benzotriazolyl]-1,1,3,3-tetramethyluronium hexafluorophosphate (HBTU, 2 mmol) in DMF:DIEA (5 mL, 4:1 v/v) for 30 min. at room temperature. After washing with DMF, the activated resin was treated with mono-Fmoc-ethylenediamine hydrochloride (1.2 mmol, 383 mg) in DMF (4 mL) containing DIEA (1.5 mmol, 261 μL) for 2 h at room temperature. 200 mg of the N-Fmoc protected resin were then deprotected with 2% DBU and 20% piperidine in DMF solution. The resulting amino group was acylated with 3-[2-(2-{2-[2-(9H-fluoren-9-ylmethoxycarbonylamino)-ethoxy]-ethoxy}-ethoxy)-ethoxy]-propionic acid (0.21 mmol, 102 mg, Quanta Biodesign, Powell, Ohio) using HBTU (0.2 mmol) in DMF:DIEA (1 mL, 9:1 v/v) for overnight at room temperature with gentle agitation. The resin was then washed with DMF and DCM, dried under vacuum and stored until use.

Synthesis of Fmoc-(1,2-dimethoxy-4-methyl-3-nitrobenzyl)-Gly-OH [Fmoc-(nitroveratryl)-Gly-OH]

The synthesis of Fmoc-(1,2-dimethoxy-4-methyl-3-nitrobenzyl)-Gly-OH for photocaging was performed as illustrated in FIG. 4A. Briefly, 6-nitroveratraldehyde (111 mg, 1 mmol), H-Gly-OH.HCl (111.5 mg, 1 mmol) and NaBH$_3$CN (126 mg, 1 mmol) were suspended in MeOH (15 mL) and stirred at 25° C. for 90 min. The suspension was concentrated to dryness in vacuo, and the residual oil was resuspended in dioxane-H$_2$O (1:1, 10 mL). Solid NaHCO$_3$ (0.26 g, 3 mmol) was added, the suspension was cooled in an ice bath, and Fmoc-OSu (0.5, 1.5 mmol) in dioxane (4 mL) was added. Stirring was continued for 90 min while cooling in an ice-bath and a 25° C. for another 90 min. The pH was adjusted to 9 by addition of solid NaHCO$_3$. The suspension was diluted with H$_2$O (40 mL) and washed with Et$_2$O (2×50 mL). Phase separations were slow, and the organic layer remained cloudy. The aqueous layer was acidified to pH 3 with 4 M aqueous HCl and extracted with EtOAc (2×50 mL). The organic phases were pooled and concentrated to dryness in vacuo. The crude material was finally purified by preparative HPLC using a linear gradient of 15-100% solvent B over 30 min to give the desired Fmoc-(nitroveratryl)-Gly-OH (300 mg, 70% overall yield). The final product was characterized by RP-HPLC and ES-MS. ES-MS [observed mass=493.0±0.1 Da; calculated for $C_{26}H_{24}N_2O_8$=492.48 Da].

Solid-Phase Peptide Synthesis of the C-Intein Polypetides.

The C-intein polypeptides are synthesized with a PEG moiety, which prevents non-specific interactions and also acts as a hydrophilic spacer, minimizing any detrimental interaction between the attached protein and the glass surface. In addition, the cystein residue in the C-extein sequence was protected with a S-tBu protecting group. This ensured that the IC-containing linker was selectively immobilized through its PEGylated terminal thiol onto the maleimido-coated glass surface The C-intein polypeptides with PEG-ylated thiol linker were manually synthesized using the HBTU activation protocol for Fmoc solid-phase peptide synthesis on resin described herein and previously described (Kwon et al (2006) Selective Immobilization of proteins onto solid supports through split-intein mediated protein trans-splicing. Angew. Chem. Int. Ed. 45:1726-1729; Camarero, et al (2004) Chemo selective attachment of biologically active proteins to surfaces by expressed protein ligation and its application for "Protein Chip" fabrication. J. Am. Chem. Soc. 126, 14730-14731). Coupling yields were monitored by the quantitative ninhydrin determination of residual free amine. Side-chain protection was employed as previously described for the Fmoc-protocol except that Fmoc-(1,2-dimethoxy-4-methyl-3-nitro-benzyl)-Gly-OH was used to photocage the corresponding Gly (residues 6, 11, 19 or 31). In addition, Fmoc-Cys(StBu)-OH was used to selectively protect Cys (residue 37).

Cloning and Expression of a Maltose Binding Protein (MBP)-N-Intein Fusion Protein.

A plasmid expressing MBP fused to the N-intein and including the 4 N-terminal extein residues (FAEY) (SEQ ID NO: 8)was created. The N-intein polypeptide sequence including the 4 N-terminal extein residues is SEQ ID NO:7.

The DNA encoding the DnaE N-intein (residues F771-K897) was isolated by PCR. The 5' primer (5'-TG GAA TTC TTT GCG GAA TAT TGC CTC AGT TTT GG-3' SEQ ID NO:1) encoded a EcoRI restriction site. The 3' oligonucleotide (5'-TTT GGA TCC TTA TTT AAT TGT CCC AGC GTC AAG TAA TGG AAA GGG-3' SEQ ID NO:2) introduced a stop codon as well as a BamHI restriction site. The PCR amplified fragment coding for the N-Intein domain was purified, digested simultaneously with EcoRI and BamHI and then ligated into a EcoRI,BamHI-treated plasmid pMAL-c2 (New England Biolabs). The resulting plasmid pMAL-N-Intein was shown to be free of mutations in the N-Intein-encoding region by DNA sequencing. Two liters of *E. coli* BL21(DE3)pLysS$^+$ cells transformed with pMAL-N-Intein plasmid were grown to mid-log phase (OD$_{600}$≈0.6) in Luria-Bertani (LB) medium and induced with 0.5 mM (isopropyl ⊕-D-thiogalactopyranoside) IPTG at 37° C. for 4 h. The lysate was clarified by centrifugation at 14,000 rpm for 30 min. The clarified supernatant (ca. 40 mL) was incubated with 5 mL of maltose-beads (New England Biolabs), previously equilibrated with column buffer (0.1 mM EDTA, 50 mM sodium phosphate, 250 mM NaCl, 0.1% Triton X-100 at pH 7.2), at 4° C. for 30 min with gently shaking. The beads were extensively washed with column buffer (10×5 mL) and equilibrated with PBS (50 mM sodium phosphate, 100 mM NaCl at pH 7.2, 2×50 mL). The MBP-fusion protein adsorbed on the beads was then eluted with column buffer containing 20 mM maltose. The filtrates were pooled, and the protein was dialyzed and concentrated.

Binding Affinities of C-intein Polypetides for MBP Fusion N-intein Polypeptides Fluorescence polarization of C-intein polypeptides upon addition of MBP-N-intein was measured at 22° C. using a JobinYvon/Spex Fluorolog 3 spectrofluorometer (Instrument S.A., Inc., Edison, N.J.) with the excitation bandwidth set at 1 nm and emission at 5 nm. The excitation wavelength for Fluorescein was set at 494 nm and emission was monitored at 514 nm. The equilibrium dissociation constant ($K_D$) for the DnaE split intein interaction was obtained by titrating a fixed concentration of C-intein polypeptides (12 nM) with increasing concentrations of MBP—N-intein in 0.5 mM EDTA, 1 mM TCEP, 50 mM sodium phosphate, 150 mM NaCl at pH 7 (high ionic strength buffer) or in 0.1 mM EDTA, 0.2 mM TCEP 10 mM sodium phosphate, 30 mM NaCl at pH 7 (low ionic strength buffer) by assuming formation of a 1:1 complex.

Measurement of Protein Trans-splicing Efficiency in Solution

In-vitro protein trans-splicing was characterized as follows. Each purified C-intein polypeptide was combined with MBP-N-intein fusion protein in splicing buffer (0.5 mM EDTA, 1 mM TCEP, 50 mM sodium phosphate, 150- 500 mM NaCl at pH 7). The concentration of the two proteins was typically in the range 0.1-200 µM. The mixture was allowed to react at 4° C. for 12-16 h. The reaction was then quenched by dilution into SDS-PAGE loading buffer containing 20% v/v 2-mercaptoethanol before the SDS-PAGE analysis. The spliced product was purified using HPLC and characterized by ES-MS as the trans-spliced product. The expected mass (average isotopic composition)=43988.0 Da; measured mass=43986±10 Da.

Functionalization of Glass Slides

The PEGylated DnaE C-intein polypeptides were immobilized onto glass slides as follows. Plain glass micro-slides (VWR Scientific Products, USA) were cleaned with RCA solution (3% $NH_3$, 3% $H_2O_2$ in water) at 80° C. for 4 h. After thorough rinsing with deionized water, the slides were washed with MeOH and treated with a 2% solution of 3-acryloxypropyl trimethoxysilane (Gelest, Morrisville, Pa.) in MeOH containing 1% $H_2O$ for 15 min. Before treating the slides, the silane solution was stirred for 10 min to allow the hydrolysis of the silane. After the silanization, the glass slides were washed with MeOH to remove excess silanol and dried under a $N_2$ stream. The adsorbed silane was then cured in the dark at room temperature under vacuum for 18 h.

Spotting Photocaged C-inteins onto Glass Slides

Standard microarray spotting techniques were used to attach proteins to modified glass slides in a microarray format. The C-intein polypeptides were diluted in spotting buffer (50 mM sodium phosphate, 100 mM NaCl buffer at pH 7.5 containing 10% glycerol) at different concentrations (20 µM-500 µM) and arrayed in the acryloxy-containing glass slides using a robotic arrayer (Norgren Systems, Palo Alto, Calif., USA). The C-intein polypeptides were spotted with a center-to-center spot distance of 350 µm with an average spot size of 200 µm in diameter. The slide was allowed to react for 18 h at room temperature. The unbound C-intein was washed and the unreacted acryloxy groups were capped using a solution of a PEGylated thiol. Imaging of C-intein polypeptide bound to the glass plate was performed as follows. The bound C-intein was reacted with 5-IAF (a thiol-reactive fluorescein derivative) and then imaged using a ScanArray 5000 (488 nm laser).

Figure 4C:
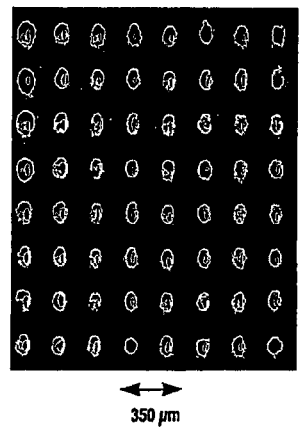
FIG. 4C is an epifluorescence image of acryloxy-coated glass slide spotted with PEGylated DnaE C-intein polypeptide (n=1, m=2 and l=3) and treated with 5-iodoacetamidofluorescein (5-IAF)

The results are shown in FIG. 4C, an epifluorescence image of acryloxy-coated glass slide spotted with PEGylated DnaE C-intein polypeptide (linker n=1, m=2 and l=3, see FIG. 4A) and treated with 5-iodoacetamidofluorescein (5-IAF).

Example 1

In order to create spatial addressable protein arrays with multiple protein components (e.g., a protein chip), a C-intein fragment was created where some of the key residues for the interaction with the N-intein were caged with a protecting group removable by UV-light, e.g., photocaged. This blocked C-intein fragment was unable to assemble with the N-intein fusion protein. When this protecting photo-labile group was removed by the action of UV-light, the two intein fragments assembled, allowing attachment of the corresponding protein to the surface through protein splicing. This methodology can be easily interfaced with cell-free protein expression systems, allowing for rapid access to the high-throughput production of protein chips.

Several DnaE C-intein polypeptides were synthesized using optimized Fmoc-based Solid-Phase Peptide Synthesis as described above. The polypeptides had identical amino acid sequences (MVKVIGRRSLGVQRIFDIGLPQDHN-FLLANGAIAANCFNK, SEQ ID NO:6) which contain the DnaE C-intein fragment residues 124-159 followed by corresponding C-extein sequences CFNK. (SEQ ID NO: 9) Each polypeptide was photocaged at a different residue: Gly6, Gly11, Gly19, Gly31, or both Gly19+Gly31. After purification by preparative HPLC the photocaged peptides were characterized by analytical HPLC and electospray mass spectrometry (ES-MS) demonstrating the C-intein polypeptides had the correct sequence, were correctly photocaged, and were pure (data not shown).

Removal of the o-nitrobenzyl backbone protecting group was efficiently accomplished by irradiating a solution of a photocaged polypeptide for with UV light at 365 nm for 30 minutes. Effective removal of the protecting group was measured by analytical HPLC and ES-MS (data not shown).

The in solution trans-splicing activity of each photocaged C-intein polypeptide was assayed using the MBP-N-intein fusion protein expressed as described above. Each photocaged C-intein polypeptide showed a significant decrease in ability to promote trans-splicing. The C-intein polypeptide with caged Gly31 was by far the most efficient singly protected C-intein in preventing trans-splicing, showing only 10% of the trans-splicing activity of the non-photocaged C-intein polypeptide. The C-intein polypeptide with caged Gly19 or Gly6 both showed about 30% of the non-photocaged trans-splicing activity. The C-intein polypeptide with caged Gly11 demonstrated around 60% of non-photocaged activity. In contrast, the C-intein polypeptide with two caged residues, Gly19 and Gly31, was able to completely prevent trans-splicing activity (data not shown)

The results demonstrate that photocaged C-intein polypeptide can be used for the creation of protein microarrays using standard photolithographic techniques similar to those employed by NimbleGen or Affimetrix for the creation of DNA microarrays, e.g. employing photomasks (Affimetrix) or Maskless Array Synthesizer (NimbleGen) technologies.

Example 2

Functionalization of Glass Slides for Use in Protein Microarrays

Glass slides coated with γ-aminopropyl-silane (GAPS IITM; Corning) are treated with 200 µL of a solution of MPS (3-maleimidopropionic acid N-hydroxysuccinimide ester, 2 mM) in 0.1 M Tris.HCl buffer at pH 7.5 for 40 min at room temperature using a hybridization chamber (Schleicher & Schuell, Keene, N.H.). The glass slides are washed with deionized H2O, MeOH, and dried under a N2 stream. The modified glass slides are immediately treated with 200 μL of a solution of thiol linkers with photocaged C-intein (0.05 mM) and without C-intein polypeptide (1.5 mM) as a control in freshly degassed 0.5 mM EDTA, 1 mM TCEP, 50 mM sodium phosphate, 150 mM NaCl buffer at pH 7.0 for 16 hours at room temperature. After the glass slides are washed and dried, the S-tBu protecting group on the C-terminal Cys residue is deprotected by treating the glass slides with 50% β-mercaptoethanol in DMF for 2 h at room temperature. The glass slides are washed with deionized H2O, MeOH, and dried under a N2 stream. The slides are used immediately or are stored for several months at −20° C.

Generation of Protein Microarrays

The glass slide is selectively deprotected at a particular spot using standard pholithographic techniques, e.g. employing photomasks (Affimetrix) or Maskless Array Synthesizer (NimbleGen) technologies. When this partially activated surface is place in contact with a solution of a particular N-intein fusion protein, the fusion protein is immobilized onto the C-intein spot previously deprotected. Once the immobilization has been completed, the unreacted N-intein fusion protein is washed away with buffer containing a high salt concentration (e.g. 10-50 sodium phosphate, 1-3 M NaCl buffer at pH 5-8). The interaction between the N-intein and the C-intein is mostly ionic. It has been described that the affinity between the DnaE N— and C-inteins is considerable weakened under high ionic conditions (Kwon et al, Angew Chem Int Ed Engl. Mar 3, 2006;45(11):1726-9 & Shi eta al, J Am Chem Soc. May 4, 2005;127(17):6198-206).

Standard microarray spotting techniques are used to attach MBP—N-intein fusion proteins to modified C-intein coated, glass slides in a microarray format. Protein solutions (0.1 μM-40 μM) of MBP—N-intein in spotting buffer (0.5 mM EDTA, 1 mM TCEP, 50 mM sodium phosphate, 150 mM NaCl buffer at pH 7.0 containing 10% glycerol) are arrayed in functionalized glass slides using a robotic arrayer (Norgren Systems). Proteins are spotted with a center-to-center spot distance of 250 μm with an average spot size of 100 μm in diameter. After spotting, the array is kept in a humidified chamber at 37° C. for 16 h. The glass substrate is thoroughly washed with PBST (50 mM sodium phosphate, 500 mM NaCl buffer at pH 7.2 containing 0.2% Triton X-100).

Immobilized MBP is detected by immunofluorescence at 543 nm using first a murine anti-MBP antibody and then a goat anti-mouse antibody conjugated to TRITC (tetramethylrhodamine isothiocyanate). The amount of fluorescence is quantified using the QuantArray software package (Packard Bioscience, Billerica, Mass., USA).

All numbers expressing quantities of ingredients, constituents, reaction conditions, and so forth used in the specification and claims are to be understood as being modified in all instances by the term "about". Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

All publications and patents mentioned in the above specification are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in organic chemistry, biochemistry, molecular biology or related fields are intended to be within the scope of the following claims.

REFERENCES

Evans, T. C. et al. (2000) Protein trans-splicing and cyclization by a naturally split intein from the dnaE gene of Synechocystis species PCC6803, J Biol Chem 275(13), 9091-4.

Perler, F. B. (1999) A natural example of protein trans-splicing, Trends Biochem Sci 24(6), 209-11.

Fields, S. (2001). Proteomics in genomeland, Science 291 (5507), 1221-4.

Gorbalenya, A. E., Non-canonical inteins, Nucleic Acids Res 26(7), 1741-8. (1998).

Lee, K. B. et al., Protein nanoarrays generated by dip-pen nanolithography, Science 295(5560), 1702-5. (2002).

Lew, B. M. et al., Protein splicing in vitro with a semisynthetic two-component minimal intein, J Biol Chem 273(26), 15887-90. (1998).

Martin, D. D. et al., Jr., Characterization of a naturally occurring trans-splicing intein from Synechocystis sp. PCC6803, Biochemistry 40(5), 1393-402. (2001).

Mills, K. V. et al., Protein splicing in trans by purified N— and C-terminal fragments of the *Mycobacterium tuberculosis* RecA intein, Proc Natl Acad Sci USA 95(7), 3543-8. (1998).

Roy, P. et al., Local photorelease of caged thymosin b4 in locomoting keratocytes causes cell turning, J. Cell Biol. 153 (5), 1035-1047 (2001).

Vossmeyer, T. et al., Combinatorial approaches toward patterning nanocrystals, J. Appl. Phys. 84(7), 3664-3670 (1998).

Wilson, D. L. et al., Surface organization and nanopatterning of collagen by dip-pen nanolithography, *Proc Natl Acad Sci USA* 98(24), 13660-4. (2001).

Wu, G. et al., Bioassay of prostate-specific antigen (PSA) using microcantilevers, Nat Biotechnol 19(9), 856-60. (2001).

Wu, H. et al., Protein trans-splicing by a split intein encoded in a split DnaE gene of *Synechocystis* sp. PCC6803, Proc. Natl. Acad. Sci. USA 95, 9226-9231 (1998).

Xu, M.-Q. et al., The mechanism of protein splicing and its modulation by mutation, EMBO J. 15(19), 5146-5153 (1996).

Zhu, H. et al., Analysis of yeast protein kinases using protein chips, Nat Genet 26(3), 283-9. (2000).

Zhu, H. et al., Global analysis of protein activities using protein chips, Science 293(5537), 2101-5. (2001).

Zhu, H. et al., Protein arrays and microarrays, Curr Opin Chem Biol 5(1), 40-5. (2001).

TABLE 1

SEQUENCES

| SEQ ID NO: | | sequence |
|---|---|---|
| 1 | Primer | 5' TG GAA TTC TTT GCG GAA TAT TGC CTC AGT TTT GG 3' |
| 2 | Primer | 5' TTT GGA TCC TTA TTT AAT TGT CCC AGC GTC AAG TAA TGG AAA GGG 3' |

TABLE 1-continued

SEQUENCES

| SEQ ID NO: | | sequence |
|---|---|---|
| 3 | N-intein Wu | CLSFGTEILTVEYGPLPIGKIVSEEINCSVYSVDP EGRVYTQAIAQWHDRGEQEVLEYELEDGSVIRATS DHRFLTTDYQLLAIEEIFARQLDLLTLENIKQTEE ALDNHRLPFPLLDAGTIK |
| 4 | C-intein Wu | MKVIGRRSLGVQRIFDIGLPQDHNFLLANGAIAAN |
| 5 | C-intein FIG. 5 | MVKVIGRRSLGVQRIFDIGLPQDHNFLLANGAIAAN CFN |

TABLE 1-continued

SEQUENCES

| SEQ ID NO: | | sequence |
|---|---|---|
| 6 | C-intein Incl. extein residues | MVKVIGRRSLGVQRIFDIGLPQDHNFLLANGAIAAN CFNK |
| 7 | N-intein incl. extein residues | FAEYCLSFGTEILTVEYGPLPIGKIVSEEINCSVY SVDPEGRVYTQAIAQWHDRGEQEVLEYELEDGSVI RATSDHRFLTTDYQLLAIEEIFARQLDLLTLENIK QTEEALDNHRLPFPLLDAGTIK |

The invention claimed is:

1. A method for producing a surface for immobilizing a polypeptide of interest to the surface wherein the polypeptide of interest is fused to an N-intein polypeptide comprising SEQ ID NO:3, comprising (a) providing a modified C-intein polypeptide comprising SEQ ID NO:4, wherein the functional amino acid side-chain of amino acid residue Asp 17 or at least one backbone amide group of amino acid residue selected from the group consisting of Gly19 and Gly31 of the modified C-intein polypeptide is protected using a 2-nitrobenzyl-based protecting group; and immobilizing the modified C-intein polypeptide to the surface; and (b) using UV-light to remove the 2-nitrobenzyl-based protecting group in order to activate the immobilized C-intein polypeptide thereby producing said surface.

2. The method of claim 1, wherein the source of UV-light is a 10 pW pulse having a wavelength of 354 nm.

3. The method of claim 1, wherein the surface is gold-based or silicon-based.

4. The method of claim 1, wherein the at least one backbone amide group of the modified C-intein polypeptide that is caged is a backbone amide group of amino acid residues Gly19 and Gly31.

5. The method of claim 1, wherein the C-intein consists of SEQ ID NO:6 and the N-intein consists of SEQ ID NO:7.

6. The method of claim 1, wherein the C-intein consists of SEQ ID NO:6 and the N-intein consists of SEQ ID NO:7 and wherein the at least one backbone amide group of the C-intein that is caged is a backbone amide group of amino acid residues Gly19 and Gly31.

7. A method for immobilizing a polypeptide of interest to at least one address on a surface, comprising (a) providing a fusion protein comprising the polypeptide of interest fused to an N-intein polypeptide comprising SEQ ID NO:3 (b) providing the surface comprising a modified C-intein polypeptide comprising SEQ ID NO:4 immobilized to the surface, wherein at least one functional amino acid side-chain of the C-intein necessary for the interaction with the N-intein is protected using a 2-nitrobenzyl-based protecting group or at least one backbone amide group of the C-intein necessary for the interaction with the N-intein protected using a 2-nitrobenzyl-based protecting group, wherein the at least one functional amino acid side-chain of the C-intein that is protected is the side chain of amino acid residue Asp 17, and wherein the at least one backbone amide group of the C-intein that is protected is the backbone amide group of amino acid residue selected from the group consisting of Gly19 and Gly31; (c) deprotecting the immobilized, modified C-intein polypeptide at the at least one address on the surface using UV-light to remove the 2-nitrobenzyl-based protecting group; and (d) contacting the fusion protein with the surface under conditions that allow trans-splicing of the C-intein and the N-intein; thereby immobilizing the polypeptide of interest to the surface at the at least one address.

8. The method of claim 7, wherein the surface is gold-based or silicon-based.

9. The method of claim 7, wherein the at least one backbone amide group of the C-intein that is caged is a backbone amide group of amino acid residues Gly19 and Gly31.

10. The method of claim 7, wherein the C-intein consists of SEQ ID NO:6 and the N-intein consists of SEQ ID NO:7.

* * * * *